United States Patent [19]

Maurer et al.

[11] 4,307,107
[45] Dec. 22, 1981

[54] ARTHROPODICIDAL N,N-DIMETHYL-O-(1,3,4-SUBSTITUTED-PYRAZOL(5)YL)-CARBAMIC ACID ESTERS

[75] Inventors: Fritz Maurer; Rolf Schröder, both of Wuppertal; Bernhard Homeyer, Leverkusen; Ingeborg Hammann, Cologne, all of Fed. Rep. of Germany

[73] Assignee: Bayer Aktiengesellschaft, Leverkusen, Fed. Rep. of Germany

[21] Appl. No.: 128,339

[22] Filed: Mar. 7, 1980

[30] Foreign Application Priority Data

Mar. 29, 1979 [DE] Fed. Rep. of Germany ....... 2912494

[51] Int. Cl.³ .................... C07D 231/20; A01N 43/56
[52] U.S. Cl. ............................. 424/273 P; 548/377; 548/367
[58] Field of Search ..................... 548/377; 424/273 P

[56] References Cited
U.S. PATENT DOCUMENTS 4,126,690 11/1978 Maurer et al. ...................... 548/377
4,215,132 7/1980 Maurer et al. ...................... 548/377

Primary Examiner—Henry R. Jiles
Assistant Examiner—Natalia Harkaway
Attorney, Agent, or Firm—Sprung, Felfe, Horn, Lynch & Kramer

[57] ABSTRACT

N,N-Dimethyl-O-(1,3,4-substituted-pyrazol(5)yl)-carbamic acid esters of the formula

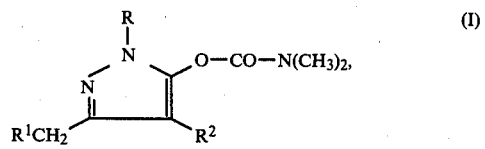

in which
R is optionally substituted alkyl, cycloalkyl or phenyl
$R^1$ is alkoxy, alkylthio, alkylsulphinyl or alkylsulphonyl, and
$R^2$ is optionally substituted alkyl
which possess insecticidal properties.

8 Claims, No Drawings

ARTHROPODICIDAL N,N-DIMETHYL-O-(1,3,4-SUBSTITUTED-PYRAZOL(5)YL)-CARBAMIC ACID ESTERS

The invention relates to certain new N,N-dimethyl-carbamic acid D-pyrazolyl esters, to a process for their preparation and to their use as agents for combating pests, especially as insecticides.

It is known that certain N,N-dimthyl-carbamic acid O-pyrazolyl esters, for example N,N-dimethyl-carbamic acid O-(1-phenyl-3-methyl-pyrazol-5-yl) ester and O-(1-isopropyl-3-methyl-pyrazol-5-yl)ester, have insecticidal properties (see Swiss patent specification No. 279,553). However, the insecticidal action of these known compounds is not always satisfactory, especially in the case of low concentrations of active compound and when small amounts are used.

The present invention now provides, as new compounds, the N,N-dimethyl-carbanic acid D-pyrazolyl esters of the general formula

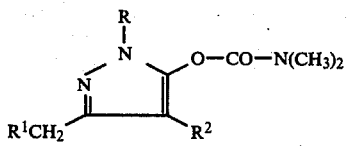

in which
R represents alkyl, cycloalkyl or phenyl, which radicals are optionally substituted,
$R^1$ represents alkoxy, alkylthio, alkylsulphinyl or alkylsulphonyl, and
$R^2$ represents optionally substituted alkyl.

Preferred compounds of the formula (I) are those in which
R represents straight-chain or branched alkyl with 1 to 8 (especially with 1 to 5) carbon atoms, cyanoethyl or cycloalkyl with 3 to 6 carbon atoms,
$R^1$ represents alkoxy, alkylthio, alkylsulphinyl or alkylsulphonyl, in each case with a straight-chain or branched alkyl radical with 1 to 5 (especially with 1 to 3) carbon atoms, and
$R^2$ represents straight-chain or branched alkyl with 1 to 5 (especially with 1 to 3) carbon atoms.

Surprisingly, the N,N-dimethyl-carbamic acid O-pyrazolyl esters according to the invention exhibit a considerably higher insecticidal action that the compounds of analogous structure and the same type of action which are already known from the state of the art.

The invention also provides a process for the preparation of an N,N-dimethyl-carbamic acid O-pyrazolyl ester of the formula (I) in which
(a) a 5-hydroxy-pyrazole of the general formula

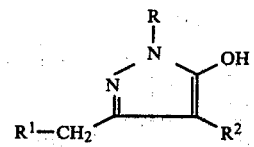

in which
R, $R^1$ and $R^2$ have the meanings indicated above, is reacted with an N,N-dimethyl-carbamic acid halide of the general formula

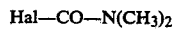

in which
Hal represents chlorine or bromine, PS if appropriate in the presence of an acid acceptor and if appropriate using an inert diluent, or (b) a 5-hydroxy-pyrazole of the general formula (II) above, in which
R, $R^1$ and $R^2$ have the meanings indicated above, is reacted with phosgene and the product is then reacted with dimethylamine, if appropriate in the presence of an acid acceptor and if appropriate using an inert diluent, or (c) provided a compound of the formula (I) is to be obtained in which R and $R^2$ have the meanings indicated above and $R^1$ is alkylsulphinyl, an N-N-dimethyl-carbamic acid O-(3-alkylthiomethyl-pyrazol-5-yl) ester of the general formula (I) in which
R and $R^2$ have the meanings indicated above and
$R^1$ represents alkylthio,
is reacted with at least an equimolar amount of hydrogen peroxide, if appropriate using a diluent, or (d) provided a compound of the formula (I), in which R and $R^2$ have the meanings indicated above and $R^1$ represents alkylsulphonyl is to be obtained, an N,N-dimethyl-carbamic acid O-(3-alkylthiomethylpyrazol-5-yl) ester of the general formula (I) in which
R and $R^2$ have the meanings indicated above and
$R^1$ represents alkylthio,
is reacted with at least two molar equivalents of m-chloroperbenzoic acid, if appropriate in the presence of a diluent, If, for example, 1-methyl-3-ethylsulphinyl-methyl-4-iso-propyl-5-hydroxy-pyrazole and dimethyl-carbamic acid chloride was used as starting substances in process variant (a) 1-cyanoethyl-3-methylsulphonylmethyl-4-ethyl-5-hydroxypyrazole, phosgene and dimethylamine are used as starting substances in process variant (b), N,N-dimethyl-carbamic acid O-(1-n-propyl-3-methyl-thiomethyl-4-n-propyl-pyrazol-5-yl) ester and hydrogen peroxide are used as starting materials in process variant (c), and N,N-dimethyl-carbamic acid O-(1-cyclopropyl-3-methylthiomethyl-4-ethyl-pyrazol-5-yl) ester and m-chloro-perbenzoic acid are used as starting materials in process variant (d), the corresponding reactions can be outlined by the following equations:

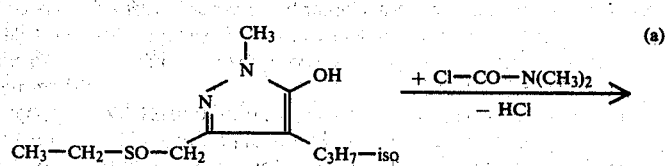

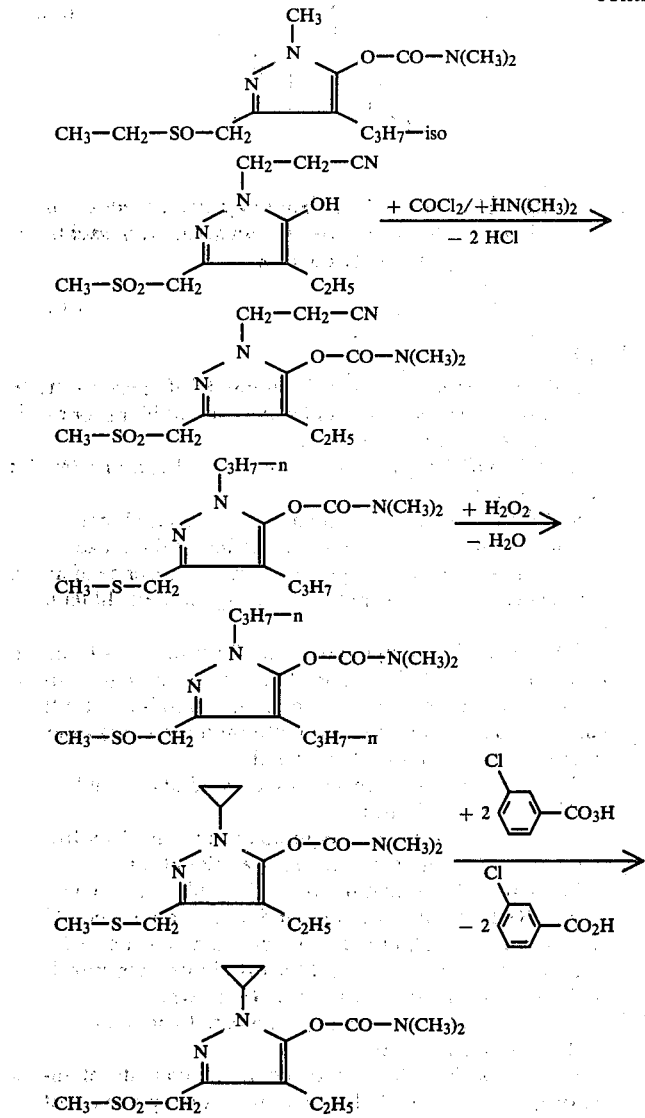

Formula (II) provides a definition of the 5-hydroxy-pyrazoles to be used as starting materials in process variants (a) and (b). In this formula, R, $R^1$ and $R^2$ preferably represent those radicals which have been mentioned as preferred in the definition of R, $R^1$ and $R^2$ in formula (I).

5-Hydroxy-pyrazoles of the formula (II) can be prepared by processes which are known in principle (see DE-OS (German Published Specification) No. 2,644,588). They are obtained, for example, by reacting γ-alkoxy-2-alkyl-or γ-alkylthio-2-alkyl-acetoacetic acid alkyl esters with hydrazine derivatives $H_2N-NHR$ (R has the meaning indicated above) at temperatures between 0° and 100° C., preferably between 20° and 80° C., if appropriate using a diluent, for example methanol.

The 3-alkylthiomethyl-5-hydroxy-pyrazoles can be oxidized, by known methods, with hydrogen peroxide to give the corresponding alkylsulphinyl compounds or with m-chloroperbenzoic acid to give the corresponding alkylsulphonyl compounds (compare preparative process vaiants (c) and (d)).

The γ-alkoxy-2-alkyl- and γ-alkylthio-2-alkylacetoacetic acid alkyl esters to be employed as precursors for the preparation of the compounds of the formula (I) are obtained by reacting γ-alkoxy- or γ-alkylthio-acetoacetic acid esters with alkylating agents, such as bromo- or iodo-alkanes or dialkyl sulphates, in the presence of a base, for example potassium tert.-butylate, if appropriate using a diluent, for example tetrahydrofuran, at temperatures between 0° and 100° C., preferably between 20° and 80° C.

γ-Alkoxy- and γ-alkylthio-acetoacetic acid esters which are employed as starting materials in this process are known (see DE-OS (German Published Specification No. 2,644,588).

Examples of the starting compounds of the formula (II) which may be mentioned are: 3-methoxymethyl-, 3-ethoxymethyl-, 3-n-propoxymethyl-, 3-iso-propoxymethyl-, 3-methylthiomethyl-, 3-ethylthiomethyl-, 3-n-propylthiomethyl-, 3-isopropylthiomethyl-, 3-methylsulphinyl-methyl-, 3-ethylsulphinylmethyl-, 3-n-propylsulphinyl-methyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4-ethyl-, -4-n-propyl- and -4-iso-propyl-1-methyl-5-hyroxy-pyrazole; 3-methoxy-methyl-, 3-ethoxymethyl-, 3-n-propoxymethyl-, 3-iso-propoxymethyl-, 3-methylthiomethyl-, 3-ethyl-thiomethyl-, 3-n-propylthiomethyl-, 3-iso-propylthio-methyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-isopropylsulphonylmethyl-4-methyl-, -4- ethyl-, -4-n-propyl- and -4-isopropyl-1-ethyl-5-hydroxy-pyrazole; 3-methoxy-methyl-, 3-ethoxymethyl-, 3-n-propoxymethyl-, 3-isopropoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4ethyl-, -4-n-propyl- and -4-iso-propyl-1-n-propyl-5-hydroxy-pyrazole; 3-methoxymethyl-, 3-ethoxymethyl-, 3-n-propoxymethyl-, 3-iso-propoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4-ethyl-, -4-n-propyl- and -4-iso-propyl-1-isopropyl-5-hydroxy-pyrazole; 3-methoxymethyl-, 3-ethoxymethyl-, 3-n-propoxymethyl-, 3-iso-propoxymethyl-, 3-methylthiomethyl-, 3-ethylthiomethyl-, 3-n-propylthiomethyl-, 3-isopropylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4-ethyl-, -4-n-propyl- and -4-iso-propyl-1-sec.-butyl-5-hydroxy-pyrazole; 3-methoxymethyl-, 3-ethoxymethyl-, 3-n-propoxymethyl-, 3-isopropoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4-ethyl-, -4-n-propyl- and -4-iso-propyl-1-tert.-butyl-5-hydroxy-pyrazole; 3-methoxy-methyl-, 3-ethoxymethyl-, 3-n-propoxymethyl-, 3-iso-propoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4-ethyl-, -4-n-propyl- and -4-isopropyl-1-(2-cyano-ethyl)-5-hydroxy-pyrazole; 3-methoxymethyl-, 3-ethoxymethyl-, 3-n-propoxymethyl-, 3-iso-propoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4-ethyl-, -4-n-propyl- and -4-iso-propyl-1-cyclopropyl-5-hydroxy-pyrazole; 3-methoxymethyl-, 3-ethoxymethyl-, 3-n-propoxymethyl-, 3-iso-propoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-isopropylsulphinylmethyl-, 3-methylsulphonylmethyl-, 3-ethylsulphonylmethyl-, 3-n-propylsulphonylmethyl- and 3-isopropylsulphonylmethyl-4-methyl-, -4-ethyl-, -4-n-propyl- and -4-iso-propyl-1-cyclobutyl-5-hydroxy-pyrazole; 3-methoxymethyl-, 3-ethoxymethyl-, 3-n-propoxymethyl-, 3-isopropoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-iso-propylsulphonylmethyl-4-methyl-, -4-ethyl-, -4-n-propyl- and -4-iso-propyl-1-cyclopentyl-5-hydroxypyrazole and 3-methoxymethyl-, 3-ethoxymethyl-, 3-n-propoxymethyl-, 3-iso-propoxymethyl-, 3-methylthiomethyl-, 3-ethylthiomethyl-, 3-n-propylthiomethyl-, 3-iso-propylthiomethyl-, 3-methylsulphinylmethyl-, 3-ethylsulphinylmethyl-, 3-n-propylsulphinylmethyl-, 3-iso-propylsulphinylmethyl-, 3-methylsulphonylmethyl-, 3-ethylsulphonylmethyl-, 3-n-propylsulphonylmethyl- and 3-isopropylsulphonylmethyl-4-methyl-, -4-ethyl-, -4-n-propyl- and -4-iso-propyl-1-cyclohexyl-5-hydroxypyrazole.

N,N-Dimethyl-carbamic acid chloride may be mentioned as an example of the carbamic acid halides of the formula (III) to be used in process variant (a). This compound has been known for a long time, as have the reactants phosgene and dimethylamine to be employed in process variant (b).

The formula (I) provides a definition of the N,N-dimethylcarbamic acid O-(3-alkylthiomethyl-pyrazol-5-yl) esters to be used as starting materials in process variants (c) and (d), with the proviso that $R^1$ represents alkylthio. Preferably, in this formula, R and $R^2$ represent those radicals which have been mentioned as preferred in the definition of the radicals R and $R^2$ in formula (I), while $R^1$ preferably represents alkylthio with 1 to 5, especially 1 to 3, carbon atoms.

Examples of these starting compounds which may be mentioned are: N,N-dimethyl-carbamic acid O-(1-methyl-3-methylthiomethyl-4-methyl-pyrazol-5-yl), O-(1-methyl-3-ethylthiomethyl-4-methyl-pyrazol-5-yl), O-(1-methyl-3-n-propylthiomethyl-4-methyl-pyrazol-5-yl), O-(1-methyl-3-iso-propylthiomethyl-4-methyl-pyrazol-5-yl), O-(1-ethyl-3-methylthiomethyl-4-methyl-pyrazol-5-yl), O-(1-ethyl-3-ethylthiomethyl-4-methyl-pyrazol-5-yl), O-(1-ethyl-3-n-propylthiomethyl-4-methyl-pyrazol-5-yl), O-(1-ethyl-3-iso-propylthiomethyl-4-methyl-pyrazol-5-yl), O-(1-n-propyl-3-methylthiomethyl-4-methyl-pyrazol-5-yl), O-(1-n-propyl-3-ethylthiomethyl-4-methyl-pyrazol-5-yl), O-(1-n-propyl-3-n-propylthiomethyl-4-methyl-pyrazol-5-yl), O-(1-n-propyl-3-iso-propylthiomethyl-4-methyl-pyrazol-5-yl), O-(1-iso-propyl-3-methylthiomethyl-4-methyl-pyrazol-5-yl), O-(1-iso-propyl-3-ethylthiomethyl-4-methyl-pyrazol-5-yl), O-(1-iso-propyl-3-n-propylthiomethyl-4-methyl-pyrazol-5-yl), O-(1-iso-propyl-3-iso-propylthiomethyl-4-methyl-pyrazol-5-yl), O-(1-(2-cyanoethyl)-3-methylthiomethyl-4-methyl-pyrazol-5-yl), O-(1-(2-cyano-ethyl)-3-ethylthiomethyl-4-methyl-pyrazol-5-yl), O-(1-(2-cyano-ethyl)-3-n-propylthiomethyl-4-methyl-pyrazol-5-yl), O-(1-(2-cyano-ethyl)-3-iso-propylthiomethyl-4-methylpyrazol-5-yl), O-(1-cyclopropyl-3-methylthiomethyl-4-methylpyrazol-5-yl), O-(1-cyclopropyl-3-ethylthiomethyl-4-methylpyrazol-5-yl), O-(1-cyclopropyl-3-n-propylthiomethyl-4-methyl-pyrazol-5-yl), O-(1-cyclopropyl-3-iso-propylthiomethyl-4-methyl-pyrazol-5-yl), O-(1-cyclopentyl-3-methylthiomethyl- 4-methyl-pyrazol-5-yl), O-(1-cyclopentyl-3-ethylthiomethyl-4-methyl-pyrazol-5-yl), O-(1-cyclopentyl-3-n-propylthiomethyl-4-methyl-pyrazol-5-yl), O-(1-cyclopentyl-3-isopropylthiomethyl-4-methyl-pyrazol-5-yl), O-(1-cyclohexyl-3-methylthiomethyl-4-methyl-pyrazol-5-yl), O-(1-cyclohexyl-3- ethylthiomethyl-4-methyl-pyrazol-5-yl), O-(1-cyclohexyl-3-n-propylthiomethyl-4-methyl-pyrazol-5-yl), O-(1-cyclohexyl-3-isopropylthiomethyl-4-methylpyrazol-5-yl), O-(1-iso-propyl-3-methylthiomethyl-4-ethyl-pyrazol-5-yl), O-(1-iso-propyl-3-methylthiomethyl-4-n-propyl-pyrazol-5-yl), O-(1-iso-propyl-3-methylthiomethyl-4-iso-propyl-pyrazol-5-yl), O-(1-(2-cyano-ethyl)-3-methylthiomethyl-4-ethyl-pyrazol-5-yl) and O-(1-(2-cyano-ethyl)-3-methylthiomethyl-4-n-propyl-pyrazol-5-yl) ester.

These alkylthio compounds of the formula (I) to be employed as starting materials can be prepared from compounds of the formula (II) wherein $R^1$ represents alkylthio according to process variant (a) or (b).

The oxidizing agents hydrogen peroxide and m-chloroperbenzoic acid to be used in process variants (c) and (d) respectively are known compounds.

Process variants (a), (b), (c) and (d) for the preparation of the N,N-dimethyl-carbamic acid O-pyrazolyl esters are preferably carried out using a diluent. Possible diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether; tetrahydrofuran and dioxane, ketones, such as acetone, methyl ethyl ketone, methyl isopropyl ketone and methyl isobutyl ketone, and nitriles, such as acetonitrile and propionitrile.

Aliphatic carboxylic acids, for example acetic acid, are also preferred solvents for process variant (c).

Process variants (a) and (b) are preferably carried out using an acid acceptor. Any of the customary acid-binding agents can be used as the acid acceptor. Alkali metal carbonates and alcoholates, such as sodium carbonate and potassium carbonate, sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

The process variants according to the invention are in general carried out at temperatures of from 0° to 100° C. The range of from 20° to 80° C. is preferred for process variants (a) and (b) and the range of from 0° to 25° C. is preferred for process variants (c) and (d). In general, the reactions are carried out under normal pressure. For carrying out process variants (a) and (b), the starting materials are usually employed in equimolar amounts. An excess of one or the other of the reaction components brings no substantial advantages. The reaction is in general carried out in a suitable diluent in the presence of an acid acceptor. When the reaction has ended the mixture is poured into water and extracted by shaking with an organic solvent, for example toluene. The organic phase is then worked up in the customary manner by washing and drying and distilling off the solvent.

The reactants are likewise preferably employed in equimolar amounts in process variant (c). The acetic acid used, as a rule, as the solvent in this process is distilled off in vacuo when the reaction has ended. An organic solvent, for example, methylene chloride, is then added and the organic phase is worked up in the customary manner by washing and drying and distilling off the solvent.

In process variant (d), the m-chloro-perbenzoic acid used as the oxidizing agent is usually employed in excess, and preferably between 2 and 3 mols are employed per mol of N,N-dimethylcarbamic acid O-(3-alkylthiomethylpyrazol-5-yl)ester. The reaction is usually carried out in a water-immiscible solvent. The mixture is then washed until neutral and worked up as described for process variant (a) and (c).

Some of the compounds according to this invention are obtained in the form of oils, some of which cannot be distilled without decomposition, but which can be freed from the last volatile constituents by so-called "incipient distillation", that is to say by prolonged heating to moderately elevated temperatures under reduced pressure, and purified in this manner. The refractive index is used for their characterization.

If the products are obtained in the solid form after distilling off the solvent, they are purified by recrystallization. The melting point is used for their characterization.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp.,

*Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Cryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetisoa,* Panonychus spp. and Tetranychus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects by the application to said animals of a compound according to the present invention, in admixture with a diluent or carrier.

The compounds of the present invention could be prepared, for example, as follows:

EXAMPLE 1

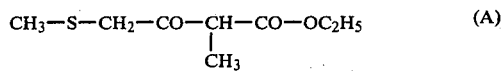

First 12.3 g (0.11 mol) of potassium tert.-butanolate and then 15.6 g (0.11 mol) of methyl iodide were added to a solution of 17.6 g (0.1 mol) of 4-methylthioacetoacetic acid ethyl ester in 100 ml of tetrahydrofuran, while cooling. The mixture was subsequently stirred at 60° C. for 12 hours, the solvent was then distilled off in vacuo, 200 ml of methylene chloride were added to the residue and the solution was extracted by shaking twice with 100 ml of water each time. The organic phase was dried over sodium sulphate and evaporated in vacuo. The residue was distilled in vacuo. 14 g (74% of theory) of 2-methyl-4-methylthioacetoacetic acid ethyl ester with a boiling point of 95°–99° C./2 mm Hg were thus obtained.

(B)

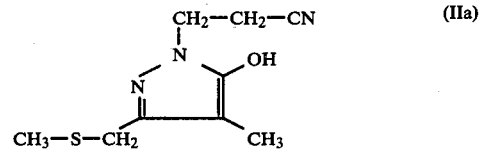

A mixture of 38 g (0.2 mol) of 2-methyl-4-methylthioacetoacetic acid ethyl ester, 17 g (0.2 mol) of 2-cyanoethyl-hydrazine and 100 ml of methanol was stirred at 60° C. for 6 hours. The solvent was then distilled off in vacuo and the residue was triturated with petroleum ether. After crystallization, the crystals were filtered off. 37 g (88% of theory) of 1-(2-cyanoethyl)-3-methyl-thiomethyl-4-methyl-5-hydroxypyrazole were obtained in this manner as a beige powder with a melting point of 98° C.

The following compounds of the formula

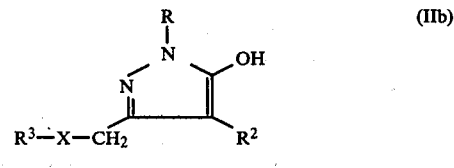

could be prepared analogously:

TABLE 1

| II | R | $R^3$ | $R^2$ | X | Yield (% of theory) | Melting point (° C.) |
|---|---|---|---|---|---|---|
| b | $CH_3$ | $CH_3$ | $CH_3$ | S | 76 | 67 |
| c | $C_3H_7$—iso | $CH_3$ | $CH_3$ | S | 47 | 84 |
| d | $C_3H_7$—iso | $CH_3$ | $CH_3$ | O | 76 | 78 |
| e | $C_3H_7$—iso | $C_2H_5$ | $CH_3$ | S | 57 | 117 |
| f | $C_3H_7$—iso | $C_3H_7$—n | $CH_3$ | S | | |
| g | $C_3H_7$—iso | $CH_3$ | $C_2H_5$ | S | 72 | viscous |
| h | $C_3H_7$—iso | $CH_3$ | $C_3H_7$—n | S | 57 | 79 |
| i | $C_2H_5$ | $CH_3$ | $CH_3$ | S | | |
| j | $C_3H_7$—n | $CH_3$ | $CH_3$ | S | | |
| k |  | $CH_3$ | $CH_3$ | S | | |
| l |  | $CH_3$ | $CH_3$ | S | | |

TABLE 1-continued

| II | R | R³ | R² | X | Yield (% of theory) | Melting point (° C.) |
|---|---|---|---|---|---|---|
| m | (phenyl) | CH₃ | CH₃ | S | | |
| n | C₄H₉—sec. | CH₃ | CH₃ | S | | |
| o | C₃H₇—iso | CH₃ | C₃H₇—iso | S | | |
| p | C₃H₇—iso | C₃H₇—iso | CH₃ | S | | |
| q | CH₂—CH₂—CN | C₂H₅ | CH₃ | S | | |
| r | CH₂—CH₂—CN | CH₃ | C₂H₅ | S | | |
| s | (phenyl) | CH₃ | CH₃ | O | | |
| t | (phenyl) | CH₃ | CH₃ | S | 80 | 117 |
| u | C₄H₉—tert. | CH₃ | CH₃ | S | | |
| v | C₄H₉—tert. | C₂H₅ | CH₃ | S | | |
| w | C₄H₉—tert. | CH₃ | C₂H₅ | S | | |

(C)

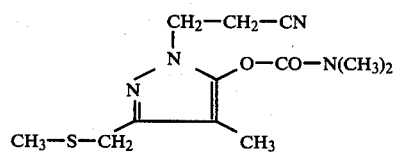

(1)

A mixture of 10.5 g (50 mmol) of 1-(2-cyanoethyl)-3-methyl-thiomethyl-4-methyl-5-hydroxy-pyrazole, 8.4 g (60 mmol) of potassium carbonate, 200 ml of acetonitrile and 5.4 g (50 mmol) of N,N-dimethyl-carbamic acid chloride was stirred at 50° C. for 12 hours. After adding 200 ml of water, the mixture was extracted with 300 ml of toluene. The organic phase was dried over sodium sulphate and was concentrated in vacuo. 12 g (85% of theory) of N,N-dimethylcarbamic acid O-(1-(2-cyanoethyl)-3-methylthiomethyl-4-methyl-pyrazol-5-yl) ester remained in the form of colorless crystals with a melting point of 78° C.

EXAMPLE 2

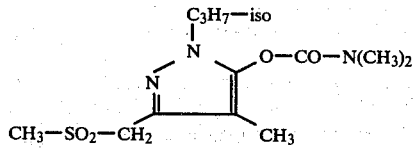

(2)

3.4 g (0.05 mol) of 50% strength hydrogen peroxide were added to a solution of 13.6 g (0.05 mol) of N,N-dimethylcarbamic acid O-(1-iso-propyl-3-methylthiomethyl-1-4-methylpyrazol-5-yl) ester in 50 ml of glacial acetic acid at 5°–10° C. The mixture was subsequently stirred at room temperature for 6 hours and the solvent was then distilled off in vacuo. The residue was dissolved in 100 ml of methylene chloride and the solution was washed with a solution of 10 g of potassium carbonate in 15 ml of water. The organic phase was separated off and dried over sodium sulphate. The solvent was then distilled off in vacuo. 12.2 g (85% of theory) of N,N-dimethyl-carbamic acid O-(1-iso-propyl-3-methyl-sulphinylmethyl-4-methyl-pyrazol-5-yl) ester were thus obtained in the form of a brown oil with a refractive index of $n_D^{20}$: 1.5222.

EXAMPLE 3

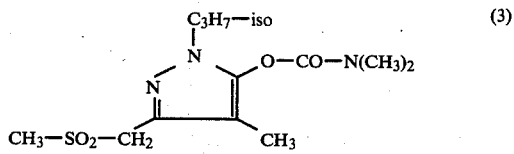

(3)

A solution of 21.3 g of m-chloroperbenzoic acid in 150 ml of chloroform was added dropwise to a solution of 13.6 g (0.05 mol) of N,N-dimethyl-carbamic acid O-(1-iso-propyl-3-methylthiomethyl-4-methyl-pyrazol-5-yl) ester in 50 ml of chloroform at 5° C. The mixture was subsequently stirred overnight at room temperature and was then filtered. The filtrate was washed with 10 ml of concentrated potassium carbonate solution and dried over sodium sulphate. The solvent was then stripped off in vacuo. 12.2 g (82% of theory) of N,N-dimethylcarbamic acid O-(1-iso-propyl-3-methylsulphonylmethyl-4-methylpyrazol-5-yl) ester remained in the form of beige crystals with a melting point of 92° C.

The following compounds of the general formula

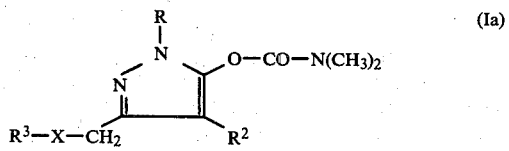

(Ia)

were each prepared analogously to one of the foregoing procedures:

TABLE 2

| Compound No. | R | R³ | R² | X | Yield (% of theory) | Melting point [°C.]; Refractive index |
|---|---|---|---|---|---|---|
| 4 | CH₃ | CH₃ | CH₃ | S | 75 | 77 |
| 5 | C₃H₇—iso | CH₃ | CH₃ | S | 93 | $n_D^{20}$:1.5149 |
| 6 | CH₂—CH₂—CN | CH₃ | CH₃ | SO | 98 | 129 |

TABLE 2-continued

| Compound No. | R | $R^3$ | $R^2$ | X | Yield (% of theory) | Melting point [°C.]; Refractive index |
|---|---|---|---|---|---|---|
| 7 | CH₂—CH₂—CN | CH₃ | CH₃ | SO₂ | 80 | 168 |
| 8 | C₃H₇—iso | CH₃ | CH₃ | O | 79 | $n_D^{20}$:1.4850 |
| 9 | C₃H₇—iso | C₂H₅ | CH₃ | S | 92 | $n_D^{20}$:1.5090 |
| 10 | C₃H₇—iso | C₃H₇—n | CH₃ | S | | |
| 11 | C₃H₇—iso | CH₃ | C₂H₅ | S | 80 | $n_D^{20}$:1.5112 |
| 12 | C₃H₇—iso | CH₃ | C₃H₇—n | S | 91 | $n_D^{20}$:1.5074 |
| 13 | C₂H₅ | CH₃ | CH₃ | S | | |
| 14 | C₃H₇—n | CH₃ | CH₃ | S | | |
| 15 |  | CH₃ | CH₃ | S | | |
| 16 |  | CH₃ | CH₃ | S | | |
| 17 |  | CH₃ | CH₃ | S | | |
| 18 | C₄H₉—sec. | CH₃ | CH₃ | S | | |
| 19 | C₃H₇—iso | CH₃ | C₃H₇—iso | S | | |
| 20 | C₃H₇—iso | C₃H₇—iso | CH₃ | S | | |
| 21 |  | CH₃ | CH₃ | SO | | |
| 22 |  | CH₃ | CH₃ | SO₂ | | |
| 23 | CH₂—CH₂—CN | C₂H₅ | CH₃ | S | | |
| 24 | CH₂—CH₂—CN | CH₃ | C₂H₅ | S | | |
| 25 | CH₂—CH₂—CN | CH₃ | C₃H₇—n | S | | |
| 26 |  | CH₃ | CH₃ | O | | |
| 27 |  | CH₃ | CH₃ | S | 82 | 68 |
| 28 | C₄H₉—tert. | CH₃ | CH₃ | S | | |
| 29 | C₄H₉—tert. | CH₃ | C₂H₅ | S | | |
| 30 | C₄H₉—tert. | C₂H₅ | CH₃ | S | | |
| 31 | C₄H₉—tert. | CH₃ | CH₃ | SO | | |
| 32 | C₄H₉—tert. | C₂H₅ | CH₃ | SO | | |
| 33 | C₄H₉—tert. | CH₃ | CH₃ | SO₂ | | |
| 34 | C₄H₉—tert. | C₂H₅ | CH₃ | SO₂ | | |

The pesticidal activity of the compounds of this invention is illustrated by the following examples wherein the compounds according to the present invention are each identified by the number (given in brackets) from the preparative examples hereinabove:

EXAMPLE 4

Myzus test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared to the prior art: (1), (2), (3), (4), (5), (8), (9), (11) and (12).

EXAMPLE 5

Test insect: Myzus persicae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (Brassica oleracea). The active compound could in this way be taken up from the soil by the plant roots and be transported into the leaves.

To demonstrate the root-systemic effect, only the leaves were infested with the above-mentioned test animals after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (4), (5), (11), (12), (1), (8), (9), (2) and (3).

It will be appreciated that the instant specification and examples are set forth by way of illustration and not limitation, and that various modifications and changes may be made without departing from the spirit and scope of the present invention.

What is claimed is:

1. An N,N-dimethyl-O-(1,3,4-substituted-pyrazol-5-yl)-carbamic acid ester of the formula

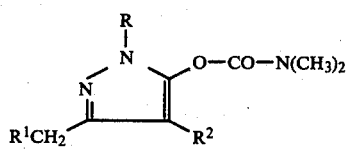

in which
R is alkyl with 1 to 8 carbon atoms optionally substituted by cyano,
$R^1$ is alkoxy, alkylthio, alkylsulphinyl or alkylsulphonyl each with 1 to 5 carbon atoms, and
$R^2$ is alkyl with 1 to 5 carbon atoms.

2. A compound according to claim 1, wherein such compound is N,N-dimethyl-O-(1-(2-cyanoethyl)-3-methylthiomethyl-4-methyl-pyrazol(5)yl)-carbamic acid ester of the formula

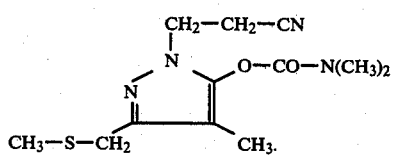

3. A compound according to claim 1, wherein such compound is N,N-dimethyl-O-(1-iso-propyl-3-methylsulfinylmethyl-4-methyl-pyrazol(5)yl)-carbamic acid ester of the formula

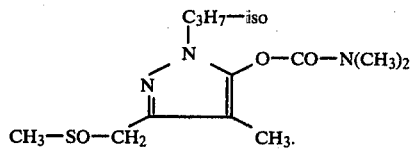

4. A compound according to claim 1, wherein such compound is N,N-dimethyl-O-(1-iso-propyl-3-methylsulfonylmethyl-4-methyl-pyrazol(5)yl)-carbamic acid ester of the formula

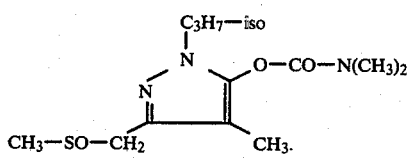

5. A compound according to claim 1, wherein such compound is N,N-dimethyl-O-(1-iso-propyl-3-methylthiomethyl-4-methyl-pyrazol(5)yl)-carbamic acid ester of the formula

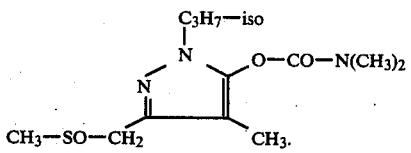

6. An arthropidicidal composition containing as active ingredient an arthropodicidally effective amount of a compound according to claim 1 in admixture with a diluent.

7. A method of combating arthropods which comprises applying to the arthropods, or to a habitat thereof, an arthropodicidally effective amount of a compound according to claim 1.

8. The method according to claim 8 in which said compound is
N,N-dimethyl-O-(1-(2-cyanoethyl)-3-methylthiomethyl-4-methyl-pyrazol(5)yl)-carbamic acid ester,
N,N-dimethyl-O-(1-iso-propyl-3-methylsulfinylmethyl-4-methyl-pyrazol(5)yl)-carbamic acid ester,
N,N-dimethyl-O-(1-iso-propyl-3-methylsulfonylmethyl-4-methyl-pyrazol(5)yl)-carbamic acid ester, or
N,N-dimethyl-O-(1-iso-propyl-3-methylthiomethyl-4-methyl-pyrazol(5)yl)-carbamic acid ester.

* * * * *

UNITED STATES PATENT AND TRADEMARK OFFICE
CERTIFICATE OF CORRECTION

PATENT NO. : 4,307,107
DATED : Dec. 22, 1981
INVENTOR(S) : Fritz Maurer et al

It is certified that error appears in the above-identified patent and that said Letters Patent are hereby corrected as shown below:

Column 18, line 19  Delete "SO" and insert $--SO_2--$.

Column 18, line 31  Delete "SO" and insert --S--.

Signed and Sealed this

Twenty-fifth Day of May 1982

[SEAL]

Attest:

Attesting Officer

GERALD J. MOSSINGHOFF

Commissioner of Patents and Trademarks